United States Patent [19]

Harris et al.

[11] 4,020,163
[45] Apr. 26, 1977

[54] USE OF HETEROCYCLIC ESTERS OF 5H-[1]BENZOPYRANO [3,4-b]PYRIDINES AS ANALGESICS

[75] Inventors: Louis Selig Harris, Richmond, Va.; Harry George Pars, Lexington, Mass.; Raj Kumar Razdan, Belmont, Mass.; John Clark Sheehan, Lexington, Mass.; Barbara Zitko Terris, Cambridge, Mass.

[73] Assignee: Sharps Associates, Cambridge, Mass.

[22] Filed: July 10, 1975

[21] Appl. No.: 594,713

Related U.S. Application Data

[62] Division of Ser. No. 434,089, Jan. 17, 1974, Pat. No. 3,905,969.

[52] U.S. Cl. .......... 424/248.55; 424/246; 424/263; 424/267; 424/274
[51] Int. Cl.[2] .......... A61K 31/44; A61K 31/54; A61K 31/445; A61K 31/535
[58] Field of Search .......... 424/248, 263, 267

*Primary Examiner*—Stanley J. Friedman
*Attorney, Agent, or Firm*—Merriam, Marshall, Shapiro & Klose

[57] ABSTRACT

Heterocyclic esters of 1,4-ethano-1,2,3,4-tetrahydro-5H-[1]benzopyrano[3,4-b]pyridines and 1,4-ethano-1,2,3,4,13,14-hexahydro-5H-[1]benzopyrano[3,4-b]pyridines. The esters have the formulas

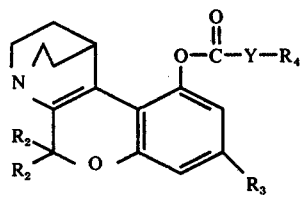

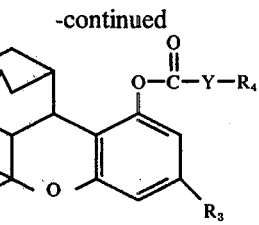

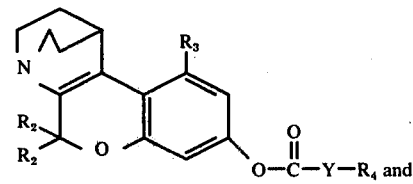

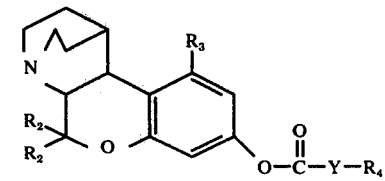

wherein $R_2$ is lower alkyl, $R_3$ is an alkyl having one to twenty carbon atoms, a cycloalkyl-lower alkyl or a phenyl-lower alkyl, Y is a straight or branched chain alkylene having one to eight carbon atoms, and $R_4$ is a group of the formula

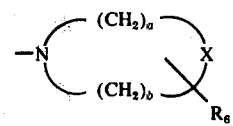

wherein a is an integer from 1 to 4, b is an integer from 1 to 4 and X is $CH_2$, O, S or N—$R_5$ with $R_5$ being hydrogen or lower alkyl, and $R_6$ is hydrogen or a lower alkyl group bonded to a carbon in the ring.

The compounds have pharmacological activity, including analgesic, anti-convulsive and tranquilizing activity in animals. The compounds can be administered in pharmaceutical composition form.

5 Claims, No Drawings

USE OF HETEROCYCLIC ESTERS OF 5H-[1]BENSOPYRANO [3,4-b]PYRIDINES AS ANALGESICS

This is a division of application Ser. No. 434,089, filed Jan. 17, 1974, now U.S. Pat. No. 3,905,969.

This invention relates to novel heterocyclic esters of 1,4-ethano-1,2,3,4-tetrahydro-5H-[1]benzopyrano[3,4-b]pyridines and 1,4-ethano-1,2,3,4,13,14-hexahydro-5H-[1]benzopyrano[3,4-b]pyridines, to methods of preparing the esters, to pharmaceutical compositions containing the esters, and to use of the esters and pharmaceutical compositions containing the compounds for pharmacological and medicinal purposes.

According to one aspect of the invention there is provided compounds of the formulae

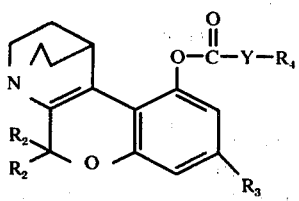

Formula 1

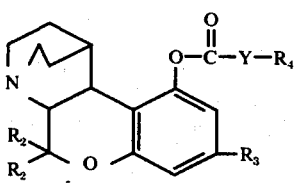

Formula 2

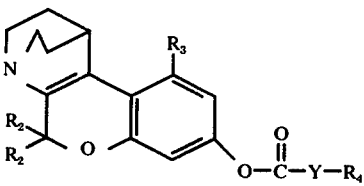

Formula 3 and

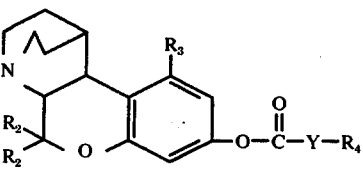

Formula 4 wherein $R_2$ is lower alkyl, $R_3$ is an alkyl having one to twenty carbon atoms, a cycloalkyl-lower alkyl or a phenyl-lower alkyl, Y is a straight or branched chain alkylene having one to eight carbon atoms, and $R_4$ is a group of the formula

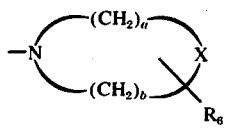

wherein $a$ is an integer from 1 to 4, $b$ is an integer from 1 to 4 and X is $CH_2$, O, S or N—$R_5$ with $R_5$ being hydrogen or lower alkyl, and $R_6$ is hydrogen or a lower alkyl group bonded to a carbon in the ring; and the nontoxic pharmaceutically acceptable acid addition salts thereof.

The term "lower alkyl" as used herein refers to straight and branched chain alkyl groups containing one to six carbons, and includes methyl, ethyl, n-propyl, isopropyl, n-butyl, sec-butyl, tert-butyl, n-pentyl, iso-pentyl, neo-pentyl and n-hexyl.

The term "cycloalkyl" as used herein refers to cyclic saturated aliphatic radicals having three to eight carbon atoms in a ring, including the cyclopropyl, cyclobutyl cyclopentyl, cyclohexyl, cycloheptyl and cyclooctyl groups.

"Cycloalkyl-lower alkyl" refers to groups having cycloalkyl and lower alkyl groups as defined above.

The term "alkyl" refers to straight and branched chain alkyl radicals having from one to twenty carbon atoms such as methyl, n-amyl, 3-methyl-2-octyl, 2-nonyl and 2-tetradecyl.

The term "phenyl-lower alkyl" refers to those groups in which lower alkyl is as defined above and "phenyl" includes this ring with or without one or more nuclear substituents such as lower alkyl groups such as methyl and ethyl, lower alkoxy groups such as methoxy and ethoxy, nitro, and halogens such as the fluoro, bromo and chloro groups.

The term "acid addition salts" refers to non-toxic salts prepared by reacting the basic esters of this invention with an organic or inorganic acid, or by reacting the esters with the salt of an appropriate acid. Representative salts which are so formed include the hydrochloride, hydrobromide, sulfate, bisulfate, acetate, valerate, oleate, laurate, borate, benzoate, lactate, phosphate, tosylate, citrate, maleate, succinate, tartrate and napsylate salts of the esters. Such salts are considered generally to be pharmaceutically acceptable.

The compounds of particular value provided by the invention are those of Formulas 1 to 4 in which $R_2$ is methyl, $R_3$ is an alkyl group having five to nine carbon atoms, or it is a phenyl-lower alkyl in which the lower alkyl has two to five carbon atoms and at least two carbons are in a chain linking the

$a$ and $b$ are the same or different integers from 1 to 3 and $a$ plus $b$ is an integer from 3 to 5; $R_6$ is hydrogen or methyl and X is $CH_2$ or O. Specifically, in such compounds $R_3$ can be 3-methyl-2-octyl or a p-fluorophenyl lower alkyl group such as 5-(p-fluorophenyl)-2-pentyl.

The 1,4-ethano-8-or-10-hydroxy-1,2,3,4-tetrahydro-5-H-[1]benzopyrano[3,4-b]pyridines and 1,4-ethano-10-hydroxy-1,2,3,4,13,14-hexahydro-5H-[1]benzopyrano[3,4-b]pyridines disclosed in U.S. Pat. 3,493,579 can be used as starting materials in making the esters of this invention. Other starting materials can be readily prepared according to the procedures disclosed in that patent by reacting an appropriate lower alkyl 3-quinuclidinone-2-carboxylate with a 5-$R_3$-resorcinol to form a 8-or-10-$R_3$-1,4-ethano-8-or-10-hydroxy-5-oxo-1,2,3,4-tetrahydro-5H-[1]benzopyrano[3,4-b]pyridine which is reacted with a Grignard reagent to produce the corresponding 5-di-lower alkyl compound. The resulting 1,2,3,4-tetrahydro compound is readily reduced catalytically to the 1,2,3,4,13,14-hexahydro compound by procedures also shown in that patent.

Some of the starting materials which can be used in this invention are the following:

- 5,5-dimethyl-1,4-ethano-10-hydroxy-8-(3-methyl-2-octyl)-1,2,3,4-tetrahydro-5H-[1]benzopyrano[3,4-b]pyridine,
- 5,5-dihexyl-1,4-ethano-10-hydroxy-8-(3-methyl-2-octyl)-1,2,3,4-tetrahydro-5H-[1]benzopyrano[3,4-b]pyridine,
- 1,4-ethano-10-hydroxy-5,5,8-trimethyl-1,2,3,4-tetrahydro-5H-[1]benzopyrano[3,4-b]pyridine,
- 5,5-dimethyl-1,4-ethano-8-hexyl-10-hydroxy-1,2,3,4-tetrahydro-5H-[1]benzopyrano[3,4-b]pyridine,
- 5,5-dipropyl-1,4-ethane-10-hydroxy-8-(2-tetradecyl)-1,2,3,4-tetrahydro-5H-[1]benzopyrano[3,4-b]pyridine,
- 5,5-dimethyl-1,4-ethano-10-hydroxy-8-(2-phenethyl)-1,2,3,4-tetrahydro-5H-[1]benzopyrano[3,4-b]pyridine,
- 8-cyclohexylethyl-5,5-dimethyl-1,4-ethano-10-hydroxy-1,2,3,4-tetrahydro-5H-[1]benzopyrano[3,4-b]pyridine,
- 5,5-dimethyl-1,4-ethano-8-hexyl-10-hydroxy-1,2,3,4,13,14-hexahydro-5H-[1]benzopyrano[3,4-b]pyridine,
- 1,4-ethano-10-hydroxy-5,5,8-trimethyl-1,2,3,4,13,14-hexahydro-5H-[1]benzopyrano[3,4-b]pyridine,
- 5,5-dihexyl-1,4-ethano-10-hydroxy-8-(3-methyl-2-octyl)-1,2,3,4,13,14-hexahydro-5H-[1]benzopyrano[3,4-b]pyridine,
- 8-cyclohexylethyl-5,5-dimethyl-1,4-ethano-10-hydroxy-1,2,3,4,13,14-hexahydro-5H-[1]benzopyrano[3,4-b]pyridine,
- 5,5-dimethyl-1,4-ethano-10-hydroxy-8-(2-phenethyl)-1,2,3,4,13,14-hexahydro-5H-[1]benzopyrano[3,4-b]pyridine,
- 1,4-ethano-8-hydroxy-5,5,10-trimethyl-1,2,3,4-tetrahydro-5H-[1]benzopyrano[3,4-b]pyridine,
- 5,5-dimethyl-1,4-ethano-10-hexyl-8-hydroxy-1,2,3,4-tetrahydro-5H-[1]benzopyrano[3,4-b]pyridine,
- 1,4-ethano-8-hydroxy-5,5,10-trimethyl-1,2,3,4,13,14-hexahydro-5H-[1]benzopyrano[3,4-b]pyridine, and
- 5,5-dimethyl-1,4-ethano-10-hexyl-8-hydroxy-1,2,3,4,13,14-hexahydro-5H-[1]benzopyrano[3,4-b]pyridine.

Generally speaking, the esters of the invention are prepared by reacting equimolar quantities of the corresponding benzopyranopyridine, a carbodiimide, such as for example dicyclohexylcarbodiimide, and the appropriate cycloamino acid, or its acid addition salt, in a suitable solvent such as methylene chloride, chloroform and the like, for from 2 to 72 hours. The mixture is then cooled in ice and filtered to remove the by-product of dicyclohexylurea.

The solvent is evaporated by, for example, employing a vacuum rotary evaporator. The product is either crystallized from suitable solvents such as benzene/ether or the residue can be chromatographed and the product isolated from the appropriate chromatographic fractions. If the basic esters are obtained, the acid addition salts can readily be prepared by reacting the ester with an appropriate organic or inorganic acid. The reaction is represented by the following reaction schemes for making the compounds:

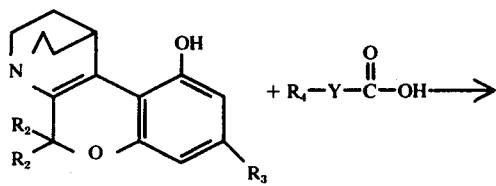 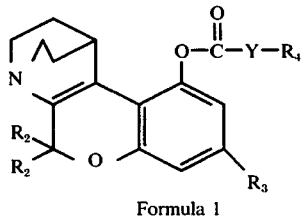

Formula 1

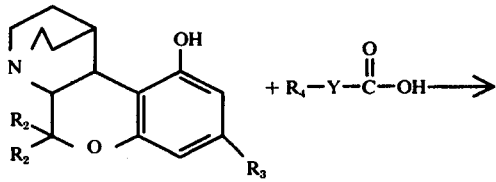 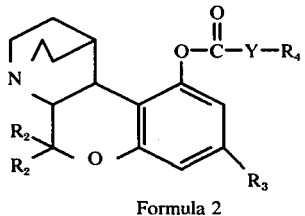

Formula 2

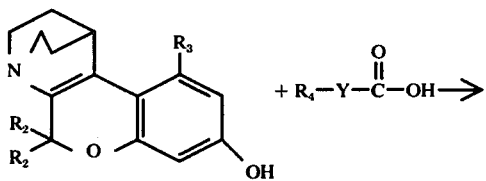 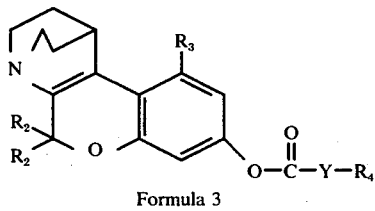

Formula 3

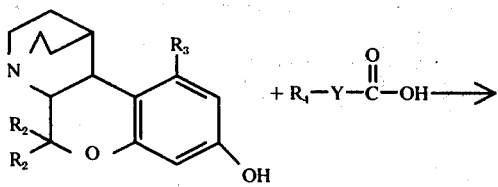 + $R_4$—Y—$\overset{\overset{O}{\|}}{C}$—OH ⟶ 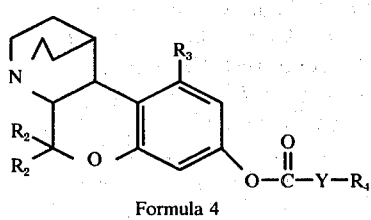

Formula 4 wherein $R_2$, $R_3$, $R_4$ and Y have the previously designated significance.

Some of the cyclicamino acids which can be used in the process of making the compounds provided by the invention are:
γ-piperidinobutyric acid,
γ-morpholinobutyric acid,
γ-(2-methylpiperidino)-butyric acid,
δ-piperidinovaleric acid,
γ-pyrrolidinobutyric acid, β-piperidinopropionic acid,
γ-thiomorpholinobutyric acid,
homopiperidinoacetic acid,
β-thiomorpholinopropionic acid and
α-methyl-γ-piperidinobutyric acid.

Patent application Ser. No. 361,897 filed May 21, 1973 disclosing such acids is incorporated herein by reference. Of course, many such acids are found in the literature.

Some of the novel esters produced according to the invention are:
5,5-dimethyl-1,4-ethano-8-(3-methyl-2-octyl)-10-[4-(piperidino)butyryloxy]-1,2,3,4-tetradhydro-5H-[1]benzopyrano-[3,4-b]pyridine,
5,5-dihexyl-1,4-ethano-8-(3-methyl-2-octyl)-10-[4-(morpholino)butyryloxy]-1,2,3,4-tetrahydro-5H-[1]benzopyrano(3,4-b]pyridine,
1,4-ethano-10-[3-(pyrrolidino)propionyloxy]-5,5,8-trimethyl-1,2,3,4-tetrahydro-5H-[1]benzopyrano[3,4-b]pyridine,
5,5-dimethyl-1,4-ethano-8-hexyl-10-[4-(thiomorpholino)-butyryloxy]-1,2,3,4-tetrahydro-5H-[1[benzopyrano[3,4-b]pyridine,
5,5-dipropyl-1,4-ethano-10-[3-(pyrrolidino)propionyloxy]-8-(2-tetradecyl)-1,2,3,4-tetrahydro-5-H[1]benzopyrano-[3,4-b]pyridine,
5,5-dimethyl-1,4-ethano-10-[4-homopiperidino)-butyryloxy]-8-(2-phenethyl)-1,2,3,4-tetrahydro-5H-[1]benzopyrano[3,4-b]pyridine,
8-cyclohexylethyl-5,5-dimethyl-1,4-ethano-10-[4-(morpholino)butyryloxy]-1,2,3,4-tetrahydro-5H-[1]benzopyrano[3,4-b]pyridine,
5,5-dimethyl-1,4-ethano-8-hexyl-10-[4-piperidino)-butyryloxy]-1,2,3,4,13,14-hexahydro-5H-[1]benzopyrano[3,4-b]pyridine,
1,4-ethano-10-[4-(morpholino)butyryloxy]-5,5,8-trimethyl-1,2,3,4,13,14-hexahydro-5H-[1]benzopyrano[3,4-b]pyridine,
5,5-dihexyl-1,4-ethano-8-(3-methyl-2-octyl)-10-[4-(piperidino)butyryloxy]-1,2,3,4,13,14-hexahydro-5H-[1]-benzopyrano[3,4-b]pyridine,
8-cyclohexylethyl-5,5-dimethyl-1,410-[3-(pyrrolidino)propionyloxy]-1,2,3,4,13,14-hexahydro-5H-[1]benzopyrano[3,4-b]pyridine,
5,5-dimethyl-1,4-ethano-8-(2-phenethyl)-[4-(thiomorpholino)butyryloxy[-1,2,3,4,13,14-hexahydro-5H-[1]benzopyrano[3,4-b]pyridine.

1,4-ethano-8-[4-(piperidino)butyryloxy]-5,5,10-trimethyl-1,2,3,4-tetrahydro-5H-[1]benzopyrano[3,4-b]pyridine,
5,5-dimethyl-1,4-ethano-10-hexyl-8-[3-(pyrrolidino)propionyloxy]-1,2,3,4-tetrahydro-5H-[1]benzopyrano[3,4-b]pyridine,
1,4-ethano-8-[4-(morpholino)butyryloxy]-5,5,10-trimethyl-1,2,3,4,13,14-hexahydro-5-H[1]benzopyrano[3,4-b]pyridine,
5,5-dimethyl-1,4-ethano-10-hexyl-8-[4-homopiperidino)butyryloxy]-1,2,3,4,13,14-hexahydro-5H-[1]benzopyrano[3,4-b]pyridine, and
the acid addition salts of such compounds, particularly the nontoxic pharmaceutically acceptable acid addition salts, including the hydrochloride, sulfate, phosphate, citrate and acetate salts thereof.

The compounds of the invention, as the free bases, can be used as acid binding agents and neutralizing agents.

The compounds of this invention when administered orally to an animal are analgesic agents. In addition, oral administration to an animal protects it from convulsions. The compounds also suppress aggressive tendencies in animals and thus can be considered as mild tranquilizing agents.

The compound 5,5-dimethyl-1,4-ethano-8-(3-methyl-2-octyl)-10-[4-morpholino)butyryloxy]-1,2,3,4-tetrahydro-5H-[1]benzopyrano[3,4-b]pyridine dihydrochloride (compound A) has marked oral activity ($ED_{50}$ = 7.3 mg./kg.) in the acetic acid induced mouse writhing test for analgesia [Brit. J. Pharmacol, 22, 246-253 (1964)]. In the rat tail flick test for analgesic activity [J. Pharmacol. Exper. Therap. 72, 74–79 (1941)]compound A at 20 mg./kg. orally increased the pain threshold 58% over the control. Compound A was found to have moderate antidepressant activity orally at 20 mg./kg. in mice in the modified DOPA potentiation test (Everett, G. M., Proc. First Internat. Sympos. Antidepressant Drugs, Excerpta Med. Int. Congr. Ser. No. 122, 1966). The compound also illustrated tranquilization activity when administered orally to mice at 10 mg./kg. through a 54% reduction in a mouse fighting test. Compound A also demonstrated anticonvulsant activity in mice; when administered orally at 30 mg./kg. to mice it gave 40% protection in the audiogenic seizure test [Plotnikoff, N. P., Pharmacol, Exp. Therap., 119, 294–298 (1957)]and in the same test at 100 mg./kg. dosage orally it gave 60% protection. A 40–60% inhibition of the tonic extensor and tonic flexor responses to supramaximal electroshock was also obtained with compound A at 100 mg./kg. dosage orally thereby further establishing anticonvulsant activity. Also, at 5 mg./kg. i.v. in mice, compound A reduced the onset time and increased the duration of halothane anesthesia thus supporting sedative activity for the compound.

The present invention includes within its scope pharmaceutical compositions comprising, as an active ingredient, at least one of the compounds of this invention, in the form of the free base or a nontoxic pharmaceutically acceptable acid addition salt, in association with a pharmaceutically acceptable carrier or diluent. The compounds of this invention exhibit oral and parenteral activity and can be formulated in dosage forms for oral, parenteral or rectal administration. Unit dosage forms can contain about 1 to 400 mg. of one or more of the compounds.

Solid dosage forms for oral administration include capsules, tablets, pills, powders and granules. In such solid dosage forms, the active compound is admixed with at least one inert diluent such as sucrose, lactose or starch. Such dosage forms can also comprise, as is normal practice, additional substances other than inert diluents, e.g., lubricating agents such as magnesium stearate, and sweetening and flavoring agents. Tablets and pills can additionally be prepared with enteric coatings.

Liquid dosage forms for oral administration include pharmaceuetically acceptable emulsions, solutions, suspensions, syrups and elixirs containing inert diluents commonly used in the art, such as water. Besides inert diluents, such compositions can also include adjuvants, such as wetting agents, emulsifying and suspending agents and sweetening, flavoring and perfuming agents.

Preparations according to this invention for parenteral administration include sterile aqueous or nonaqueous solutions, suspensions or emulsions. Examples of non-aqueous solvents or vehicles are propylene glycol, polyethylene glycol, vegetable oils such as olive oil, and injectable organic esters such as ethyl oleate. Such dosage forms may also contain adjuvants such as preserving, wetting, emulsifying and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal administration are suppositories which may contain, in addition to the active substance, excipients such as cocoa butter or a suppository wax.

The dosage of active ingredient in the compositions of this invention may be varied; however, it is necessary that the amount of the active ingredient shall be such that a suitable dosage form is obtained. The selected dosage depends upon the desired therapeutic effect, on the route of administration and on the duration of the treatment. Generally, dosage levels of between 1 to 40 mg./kg. of body weight daily are administered to patients in need of analgesia or tranquilization.

The following is an illustration of the pharmaceutical compositions which are a feature of this invention:

Tablet Composition

Tablets weighing 196 mg. and having the following composition are prepared by standard tableting procedures:

| Ingredient | Mg. |
|---|---|
| 5,5-Dimethyl-1,4-ethano-8-(3-methyl-2-octyl)-10-[4-(morpholino)butyryloxy]-1,2,3,4-tetrahydro-5H-[1]benzopyrano[3,4-b]pyridine dihydrochloride | 100 |
| Starch | 90 |
| Colloidal silica | 5 |
| Magnesium stearate | 1 |

It will be understood by those skilled in the art that the above composition can contain any of the compounds of this invention.

The following examples further illustrate the present invention:

EXAMPLE 1

5,5-Dimethyl-1,4-ethano-8-(3-methyl-2-octyl)-10-[4-(morpholino)-butyryloxy]-1,2,3,4-tetrahydro-5H-[1]benzopyrano[3,4-b]pyridine dihydrochloride

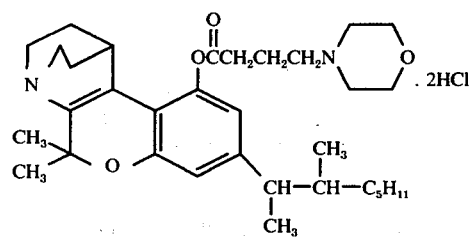

A mixture of 3.0 g. (7.8 mmole) of 5,5-dimethyl-1,4-ethano-10-hydroxy-8-(3-methyl-2-octyl)-1,2,3,4-tetrahydro-5H-[1]benzopyrano[3,4-b]pyridine, 1.64 g. (7.8 mmole) of γ-morpholinobutyric acid hydrochloride (J. Am. Chem. Soc. 83, 2891 (1961) and 1.7 g. (8.25 mmole) of dicyclohexylcarbodiimide in 150 ml. of methylene chloride was stirred at room temperature for 16 hours. After cooling the reaction mixture, the byproduct of dicyclohexylurea was removed by suction filtration. The solvent was removed by means of a rotary evaporator to give a colorless, tacky residue which was dissolved in diethyl ether and converted to the dihydrochloride by the addition of ethereal hydrogen chloride. The material crystallized from an acetonitrile/ether mixture to give 2.35 g. (47%) of colorless solid. The sample was pure by thi- layer chromatography and the infrared and nuclear magnetic resonance spectra are in agreement with the proposed structure.

Anal. Calcd. for $C_{33}H_{52}Cl_2N_2O_4 \cdot 1/2H_2O$ (MW=620.65). C, 63.86; H, 8.45; N, 4.51;

Found: C, 63.93; H, 8.51; N, 4.58.

EXAMPLE 2

5,5-Dimethyl-1,4-ethano-8-(3-methyl-2-octyl)-10-[4-(piperidino)butyryloxy]-1,2,3,4-tetrahydro-5H-[1]benzopyrano[3,4-b]pyridine dihydrochloride 5,5-Dimethyl-1,4-ethano-10-hydroxy-8-(3-methyl-2-octyl)-1,2,3,4-tetrahydro-5H-[1]benzopyrano[3,4-b]pyridine is reacted with γ-piperidinobutyric acid hydrochloride according to Example 1 to produce 5,5-dimethyl-1,4-ethano-8-(3-methyl-2-octyl)-10-[4-(piperidino)butyryloxy]-1,2,3,4-tetrahydro-5H-[1]benzopyrano[3,4-b]pyridine dihydrochloride.

EXAMPLE 3

5,5-Diethyl-1,4-ethano-10-[4-(2-methylpiperidino)-butyryloxy]-8-(3-methyl-2-octyl)-1,2,3,4-tetrahydro-5H-[1]benzopyrano[3,4-b]pyridine hydrochloride 5,5-Diethyl-1,4-ethano-10-hydroxy-8-(3-methyl-2-octyl)-1,2,3,4-tetrahydro-5H-[1]benzopyrano[3,4-b]pyridine is reacted with γ-(2-methylpiperidino)-butyric acid hydrochloride to produce 5,5-diethyl-1,4-ethano-10-[4-(2-methylpiperidino)-butyryloxy]-8-(3-methyl-2-octyl)-1,2,3,4-tetrahydro-5H-[1]benzopyrano[3,4-b]pyridine hydrochloride.

EXAMPLE 4

5,5-Dipropyl-1,4-ethano-8-pentyl-10-[5-(piperidino)-valeryloxy]-1,2,3,4-tetrahydro-5H-[1]benzopyrano[3,4-b]pyridine 5,5-Dipropyl-1,4-ethano-10-hydroxy-8-pentyl-1,2,3,4-tetrahydro-5H-[1]benzopyrano[3,4-b]pyridine is reacted with δ-piperidinovaleric acid to produce 5,5-dipropyl-1,4-ethano-8-pentyl-10-[5-(piperidino)-valeryloxy]-1,2,3,4-tetrahydro-5H-[1]benzopyrano[3,4-b]pyridine.

EXAMPLE 5

5,5-Dimethyl-8-(2-cyclohexylethyl)-1,4-ethano-10-[4-pyrrolidino)-butyryloxy]-1,2,3,4-tetrahydro-5H-[1]benzopyrano[3,4-b]pyridine 5,5-Dimethyl-8-(2-cyclohexylethyl)-1,4-ethano-10-hydroxy-1,2,3,4-tetrahydro-5H-[1]benzopyrano[3,4-b]pyridine is reacted with δ-pyrrolidinobutyric acid to produce 5,5-dimethyl-8-(2-cyclohexylethyl)-1,4-ethano-10-[4-pyrrolidino)-butyryloxy]-1,2,3,4-tetrahydro-5H-[1]benzopyrano[3,4-b]pyridine.

EXAMPLE 6

5,5-Dimethyl-1,4-ethano-8-(3-methyl-2-octyl)-10-[4-(thiomorpholino)-butyryloxy]-1,2,3,4-tetrahydro-5H-[1]benzopyrano[3,4-b]pyridine dihydrochloride 5,5-Dimethyl-1,4-ethano-10-hydroxy-8-(3-methyl-2-octyl)-1,2,3,4-tetrahydro-5H-[1]benzopyrano[3,4-b]pyridine is reacted with δ-thiomorpholinobutyric acid hydrochloride according to Example 1 to produce 5,5-dimethyl-1,4-ethano-8-(3-methyl-2-octyl)-10-[4-(thiomorpholino)butyryloxy]-1,2,3,4-tetrahydro-5H-1]benzopyrano[3,4-b]pyridine dihydrochloride.

EXAMPLE 7

5,5-Dibutyl-1,4-ethano-10-[2-(homopiperidino)acetoxy]-8-tetradecyl-1,2,3,4-tetrahydro-5H-[1]benzopyrano[3,4-b]pyridine dihydrochloride 5,5-Dibutyl-1,4-ethano-10-hydroxy-8-tetradecyl-1,2,3,4-tetrahydro-5H-[1]benzopyrano[3,4-b]pyridine is reacted with homopiperidinoacetic acid hydrochloride according to Example 1 to produce 5,5-dibutyl-1,4-ethano-10-[2-(homopiperidino)-acetoxy]-8-tetradecyl-1,2,3,4-tetrahydro-5H-[1]benzopyrano[3,4-b]pyridine dihydrochloride.

EXAMPLE 8

10-[4-(Azetidino)butyryloxy]-5,5-dimethyl-1,4-ethano-8-(3-methyl-2-octyl)-1,2,3,4-tetrahydro-5H-[1]benzopyrano[3,4-b]pyridine hydrobromide 5,5-Dimethyl-1,4-ethano-10-hydroxy-8-(3-methyl-2-octyl)-1,2,3,4-tetrahydro-5H-[1-benzopyrano(3,4-b]pyridine is reacted with γ-azetidinobutryic acid hydrobromide to produce 10-[4-(azetidino)-butyryloxy]-5,5-dimethyl-1,4-ethano-8-(3-methyl-2-octyl)-1,2,3,4-tetrahydro-5H-[1]benzopyrano[3,4-b]pyridine hydrobromide.

EXAMPLE 9

1,4-Ethano-10-[3-(piperidino)propionyloxy]-5,5,8-trimethyl-1,2,3,4-tetrahydro-5H-[1]benzopyrano[3,4-b]pyridine 1,4-Ethano-10-hydroxy-5,5,8-trimethyl-1,2,3,4-tetrahydro-5H-[1]benzopyrano[3,4-b]pyridine is reacted with β-piperidino-propionic acid is produce 1,4-ethano-10-[3-(piperidino) propionyloxy]-5,5,8-trimethyl-1,2,3,4-tetrahydro-5H-[1]benzopyrano[3,4-b]pyridine.

EXAMPLE 10

5,5-Dihexyl-1,4-ethano-10-[2-methyl-4-(morpholino)-butyryloxy]-8-(3-methyl-2-octyl)-1,2,3,4-tetrahydro-5H-[1]benzopyrano[3,4-b]pyridine hydrobromide 5,5-Dihexyl-1,4-ethano-10-hydroxy-8-(3-methyl-2-octyl)-1,2,3,4-tetrahydro-5H-[1]benzopyrano[3,4-b]pyridine is reacted with 2-methyl-4-(morpholino)-butyric acid hydrobromide to produce 5,5-dihexyl-1,4-ethano-10-[2-methyl-4-(morpholino)butyryloxy]-8-(3-methyl-2-octyl)-1,2,3,4-tetrahydro-5H-[1]benzopyrano[3,4-b]pyridine hydrobromide.

EXAMPLE 11

8-[3-(Cyclopentyl)propyl]-5,5-dimethyl-1,4-ethano-10-[4-(morpholino)butyryloxy]-1,2,3,4-tetrahydro-5H-[1]benzopyrano [3,4-b]pyridine 8-[3-(Cyclopentyl)propyl]-5,5-dimethyl-1,4-ethano-10-hydroxy-1,2,3,4-tetrahydro-5H-[1]benzopyrano[3,4-b]pyridine is reacted with γ-morpholinobutyric acid to produce 8-[3-(cyclopentyl)-propyl]-5,5-dimethyl-1,4-ethano-10-[4-(morpholino) butyryloxy]-1,2,3,4-tetrahydro-5H-[1]benzopyrano[3,4-b]pyridine.

EXAMPLE 12

5,5-Dihexyl-1,4-ethano-8-(3-methyl-2-octyl)-10-[4-(morpholino)butyryloxy]-1,2,3,4,13,14-hexahydro-5H-[1]benzopyrano[3,4-b]pyridine hydrochloride 5,5-Dihexyl-1,4-ethano-10-hydroxy-8-(3-methyl-2-octyl-1,2,3,4,13,14-hexahydro-5H-[1]benzopyrano[3,4-b]pyridine is reacted with γ-morpholinobutyric acid hydrochloride to produce 5,5-dihexyl-1,4-ethano-8-(3-methyl-2-octyl)-10-[4-(morpholino)-butyryloxy]-1,2,3,4,13,14-hexahydro-5H-[1]benzopyrano[3,4-b]pyridine hydrochloride.

EXAMPLE 13

1,4-Ethano-10-[4-(piperidino)butyryloxy]-5,5,8-trimethyl-1,2,3,4,13,14-hexahydro-5H-[1]benzopyrano[3,4-b]pyridine 1,4-Ethano-10-hydroxy-5,5,8-trimethyl-1,2,3,4,13,14-hexahydro-5H-[1]benzopyrano[3,4-b]pyridine is reacted with γ-piperidinobutyric acid to produce 1,4-ethano-10-[4-(piperidino)-butyryloxy-5,5,8-trimethyl-1,2,3,4,13,14-hexahydro-5H-[1]benzopyrano[3,4-b]pyridine.

EXAMPLE 14

5,5-Dimethyl-1,4-ethano-8-hexyl-10-[4-(pyrrolidino)-butyryloxy]-1,2,3,4,13,14-hexahydro-5H-[1]benzopyrano-[3,4-b]pyridine 5,5-Dimethyl-1,4-ethano-8-hexyl-10-hydroxy-1,2,3,4,13,14-hexahydro-5H-[1]benzopyrano[3,4-b]pyridine is reacted with γ-pyrrolidinobutyric acid to produce 5,5-dimethyl-1,4-ethano-8-hexyl-10-[4-(pyrrolidino)butyryloxy[-1,2,3,4,13,14-hexahydro-5H-[1]benzopyrano-[3,4-b]pyridine.

EXAMPLE 15

5,5-Dimethyl-1,4-ethano-8-(3-methyl-2-octyl)-10-[4-(thiomorpholino)-butyryloxy]-1,2,3,4,13,14-hexahydro-5H-[1]benzopyrano[3,4-b]pyridine dihydrochloride 5,5-Dimethyl-1,4-ethano-10-hydroxy-8-(3-methyl-2-octyl)-1,2,3,4,13,14-hexahydro-5H-[1]benzopyrano[3,4-b]pyridine is reacted with γ-thiomorpholinobutyric acid hydrochloride according to Example 1 to produce 5,5-dimethyl-1,4-ethano-8-(3-methyl-2-octyl)-10-[4-(thiomorpholino)butyryloxy]1,2,3,4,13,14-hexahydro-5H-[1]benzopyrano[3,4-b]pyridine dihydrochloride.

EXAMPLE 16

5,5-Dibutyl-1,4-ethano-10-[2-(homopiperidino)acetoxy]-8-tetradecyl-1,2,3,4,13,14-hexahydro-5H-[1]benzopyrano[3,4-b]pyridine 5,5-Dibutyl-1,4-ethano-10-hydroxy-8-tetradecyl-1,2,3,4,13,14-hexahydro-5H-[1]benzopyrano[3,4-b]pyridine is reacted with homopiperidinoacetic acid to produce 5,5-dibutyl-1,4-ethano-10-[2-(homopiperidino)acetoxy]-8-tetradecyl-1,2,3,4,13,14-hexahydro-5H-[1]benzopyrano[3,4]pyridine.

EXAMPLE 17

1,4-Ethano-8-[4-(fluorophenyl)-1-methylbutyl]-10-hydroxy-5-oxo-1,2,3,4-tetrahydro-5H[1]benzopyrano[3,4-b]pyridine hydrochloride Ethyl 3-quinuclidinone-2-carboxylate hydrochloride (20.0 g.) is added in portions to 22.9 g. of 5-[4-(4-fluorophenyl)-1-methylbutyl]resorcinol in 37 ml. of methanesulfonic acid and 24 ml. of phosphorous oxychloride. The mixture is stirred at room temperature for 5 days. To the stirred mixture is added 20 ml. of chloroform and 200 ml. of water The reaction mixture is stirred for 20 minutes whereupon three layers form. The water layer is removed and the mixture extracted with more water. The middle layer is then removed and concentrated in vacuo. The addition of acetonitrile produces a solid which is crystallized from tetrahydrofuran to yield 16.4 g. of the intermediate as a white solid, m.p. 271°–281° C., which produces one spot in thin layer chromatography.

Anal. Calcd. for $C_{25}H_{27}ClFNO_3$. C, 67.55; H, 6.14; N, 3.15; Cl, 8.00;

Found: C, 67.63; H, 6.22; N, 3.10; Cl, 7.98

EXAMPLE 18

5,5-Dimethyl-1,4-ethano-8[4-(4-fluorophenyl)-1-methylbutyl]-10-hydroxy-1,2,3,4-tetrahydro-5H[1]benzopyrano[3,4-b]pyridine hydrobromide 1,4-Ethano-8-[4-(4-fluorophenyl)-1-methylbutyl]-10-hydroxy-5-oxo-1,2,3,4-tetrahydro-5H[1]benzopyrano[3,4-b]pyridine hydrochloride (13 g.) is stirred with chloroform, water and potassium bicarbonate for 30 minutes. The chloroform layer is separated and evaporated in vacuo. The concentrate is taken up in benzene, concentrated to dryness, dissolved in 80 ml. of anisole and added to a solution of 100 ml. of 3 molar methyl magnesium bromide in ether and 100 ml. of anisole. The reaction is stirred under a nitrogen atmosphere at 37° C. for 18 hours. Water (60 ml.) is slowly added to the reaction mixture while cooling, followed by 80 ml. of 20% sulfuric acid. The anisole is removed by steam distillation, and the resulting solid is recrystallized from acetonitrile to yield 10.7 g. of product, m.p. 284–286° C.

Anal. Calcd. for $C_{27}H_{33}BrFNO_2$. C, 64.19; H, 6.63; N, 2.78;

Found: C, 64.00; H, 6.74; N, 2.82.

EXAMPLE 19

1,4-Ethano-10-hydroxy-8-(1-methyl-4-phenylbutyl)-5-oxo-1,2,3,4-tetrahydro-5H[1]benzopyrano[3,4-b]pyridine hydrobromide Following a procedure similar to that described in Example 17, 1,4-ethano-10-hydroxy-8-(1-methyl-4-phenylbutyl)-5-oxo-1,2,3,4-tetrahydro-5H[1]benzopyrano[3,4-b]pyridine is prepared by reacting 3-quinuclidinone-2-carboxylate with 5-(1-methyl-4-phenylbutyl)resorcinol in the presence of methanesulfonic acid and phosphorus oxychloride.

EXAMPLE 20

5,5-Dimethyl-1,4-ethano-10-hydroxy-8-(1-methyl-4-phenylbutyl)1,2,3,4-tetrahydro-5H[1]benzopyrano[3,4-b]pyridine 5,5-Dimethyl-1,4-ethano-10-hydroxy-8-(1-methyl-4-phenylbutyl)-1,2,3,4-tetrahydro-5H[1]benzopyrano[3,4-b]pyridine is prepared following a procedure similar to that described in Example 18 by reacting 1,4-ethano-10-hydroxy-8-(1-methyl-4-phenylbutyl)-5-oxo-1,2,3,4-tetrahydro-5H[1]benzopyrano[3,4-b]pyridine with methyl magnesium bromide in anisole.

EXAMPLE 21

5,5-Dimethyl-1,4-ethano-8-[4-(4-fluorophenyl)-1-methylbutyl]-10-[4-(morpholino)butyryloxy]-1,2,3,4-tetrahydro-5H-[1]benzopyrano[3,4-b]pyridine hydrochloride 5,5-Dimethyl-1,4-ethano-8-[4-(4-fluorophenyl)-1-methylbutyl]-10-hydroxy-1,2,3,4-tetrahydro-5H[1]benzopyrano [3,4-b]pyridine is reacted with γ-morpholinobutyric acid hydrochloride in the presence of dicyclohexylcarbodiimide to produce 5,5-dimethyl-1,4-ethano-8-[4-(4-fluorophenyl)-1-methylbutyl]-10-[4-morpholino)butyryloxy]-1,2,3,4-tetrahydro-5H-[1benzopyrano[3,4-b]pyridine hydrochloride.

EXAMPLE 22

5,5-Dimethyl-1,4-ethano-8-(1-methyl-4-phenylbutyl)-10-[4-(piperidino)butyryloxy]-1,2,3,4-tetrahydro-5H-[1]benzopyrano [3,4-b]pyridine hydrochloride 5,5-Dimethyl-1,4-ethano-10-hydroxy-8-(1-methyl-4-phenylbutyl)-1,2,3,4-tetrahydro-5H-[1]benzopyrano[3,4-b]pyridine is reacted with γ-piperidinobutyric acid hydrochloride in the presence of dicyclohexycarbodiimide to produce 5,5-dimethyl-1,4-ethano-8-(1-methyl-4-phenylbutyl)-10-[4-(piperidino)-butyryloxy]-1,2,3,4-tetrahydro-5H-[1]benzopyrano[3,4-b]pyridine hydrochloride.

The foregoing detailed description has been given for clearness of understanding only, and no unnecessary limitations should be understood therefrom, as modifications will be obvious to those skilled in the art.

What is claimed is:

1. A method which comprises administering to an animal, to induce an analgesic effect in the animal, a compound of the formulas

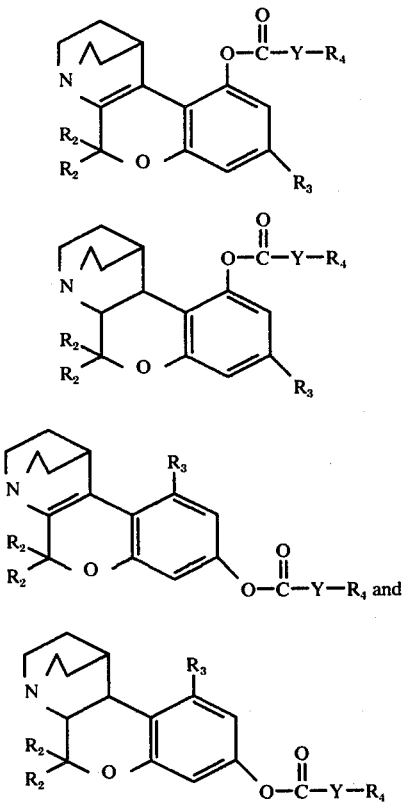

wherein $R_2$ is lower alkyl, $R_3$ is an alkyl having one to twenty carbon atoms, a cycloalkyl-lower alkyl or a phenyl-lower alkyl, Y is a straight or branched chain alkylene having one to eight carbon atoms, and $R_4$ is a group of the formula

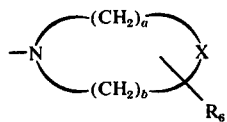

wherein $a$ is an integer from 1 to 4, $b$ is an integer from 1 to 4 and X is $CH_2$, O, S or N-$R_5$ with $R_5$ being hydrogen or lower alkyl, and $R_6$ is hydrogen or a lower alkyl group bonded to a carbon in the ring, or a nontoxic pharmaceutically acceptable acid addition salt thereof, in an amount which is safe and effective in inducing an analgesic effect in the animal.

2. A method according to claim 1 in which about 1 to 400 mg. of the compound is administered.

3. A method according to claim 1 in which the compound is 5,5-dimethyl-1,4-ethano-8-(3-methyl-2-octyl)-10-[4-(morpholino)butyryloxy]-1,2,3,4-tetrahydro-5H-[1] benzopyrano[3,4-b]pyridine.

4. A pharmaceutical composition in unit dosage form comprising about 1 to 400 mg. of a compound of the formulas

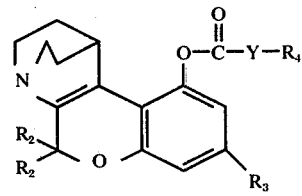

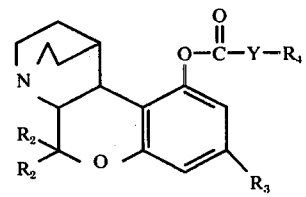

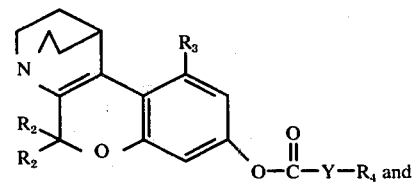

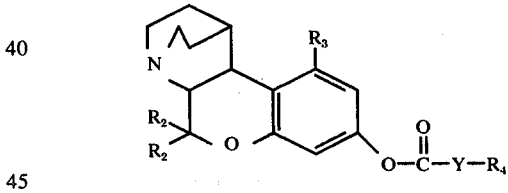

wherein $R_2$ is a lower alkyl, $R_3$ is an alkyl having one to twenty carbon atoms, a cycloalkyl-lower alkyl or a phenyl-lower alkyl, Y is a straight or branched chain alkylene having one to eight carbon atoms, and $R_4$ is a group of the formula

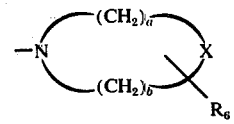

wherein $a$ is an integer from 1 to 4, $b$ is an integer from 1 to 4 and X is $CH_2$, O, S or N-$R_5$ with $R_5$ being hydrogen or lower alkyl, and $R_6$ is hydrogen or a lower alkyl group bonded to a carbon in the ring, or a nontoxic pharmaceutically acceptable acid addition salt thereof, and a pharmaceutically acceptable carrier.

5. A pharmaceutical composition according to claim 4 in which the compound is 5,5-dimethyl-1,4-ethano-8-(3-methyl-2-octyl)-10-[4-(morpholino)butyryloxy]-1,2,3,4-tetrahydro-5H-[1]benzopyrano[3,4-b]pyridine.

* * * * *

UNITED STATES PATENT AND TRADEMARK OFFICE
CERTIFICATE OF CORRECTION

PATENT NO. : 4,020,163
DATED : April 26, 1977
INVENTOR(S) : Louis Selig Harris et al.

It is certified that error appears in the above-identified patent and that said Letters Patent are hereby corrected as shown below:

Column 2, line 11, insert a comma (,) after "butyl", line 41, after "two" first occurrence insert -- to nine carbo and the phenyl is substituted or unsubstituted, Y is a straight or branched alkylene having two--; column 3, line 14, change "ethane" to --ethano--; column 5, line 34, change "tetradhydro" to --tetrahydro--, line 63, change "1,410" to -- 1,4-ethano-10 --; column 6, line 39, change "4-" to -- 4-( --; column 7, line 29, change "suspensing" to --suspending--; column 8, line 49, change "thi-" to --thin--; column 10, line 23, change "is" to --to--; column 11, line 9, change "butyryloxy-" to -- butyryloxy]- --, line 22, change "[" to --]--, line 37, insert a dash (-) before "1,2", line 49, change "[3,4]" to --[3,4-b]--, line 52, change "4-(" to -- 4-(4- --, line 62, place a period (.) after "water"; column 13, line 2, change "[1" to --[1]--.

Signed and Sealed this ninth Day of August 1977

[SEAL]

Attest:

RUTH C. MASON
Attesting Officer

C. MARSHALL DANN
Commissioner of Patents and Trademar